United States Patent [19]

Peter et al.

[11] Patent Number: 5,051,523
[45] Date of Patent: Sep. 24, 1991

[54] PROCESS FOR THE PREPARATION OF COMPLEX COMPOUNDS

[75] Inventors: Heinrich H. Peter, Binningen; Théophile Moerker, Füllinsdorf, both of Switzerland

[73] Assignee: Ciba-Geigy Corporation, Ardsley, N.Y.

[21] Appl. No.: 296,561

[22] Filed: Jan. 13, 1989

[30] Foreign Application Priority Data

Jan. 20, 1988 [CH]  Switzerland ............................ 184/88

[51] Int. Cl.$^5$ .......................... C07F 5/00; C07F 13/00; C07F 15/00
[52] U.S. Cl. ......................................... 556/148; 556/1; 556/41; 556/50; 556/116; 556/138; 556/146
[58] Field of Search ...................... 556/148, 146, 1, 41, 556/50, 116, 138; 534/14, 10; 424/1.1, 9

[56] References Cited

U.S. PATENT DOCUMENTS

| | | | |
|---|---|---|---|
| 3,634,407 | 1/1972 | Gaeumann et al. | 260/239.3 |
| 4,406,905 | 9/1983 | Zähner et al. | 424/263 |
| 4,637,929 | 1/1987 | Quay | 424/9 |
| 4,645,660 | 2/1987 | Takahashi et al. | 424/1.1 |
| 4,687,658 | 8/1987 | Quay | 556/148 X |
| 4,707,352 | 11/1987 | Stavrianpoulos | 424/1.1 |
| 4,714,607 | 12/1987 | Klaveness | 556/148 X |
| 4,758,422 | 7/1988 | Quay | 424/9 |

FOREIGN PATENT DOCUMENTS

| | | |
|---|---|---|
| 45281 | 2/1981 | European Pat. Off. . |
| 232751 | 8/1987 | European Pat. Off. . |
| 235361 | 9/1987 | European Pat. Off. . |

Primary Examiner—Arthur C. Prescott
Attorney, Agent, or Firm—Irving M. Fishman; JoAnn Villamizer

[57] ABSTRACT

There is disclosed a process for the preparation of analytically pure chelate complexes which can be used in diagnostic medicine, for example as contrast media or radiopharmaceuticals. The process comprises transcomplexing a complex of a β-dicarbonyl compound and a metal ion, for example a metal acetylacetonate, which is readily soluble in an organic solvent that is not miscible in all proportions with water, with a stoichiometric amount or with a less than equivalent amount of a chelating agent whose binding affinity for the metal ion is greater than that of the β-dicarbonyl compound.

14 Claims, No Drawings

PROCESS FOR THE PREPARATION OF COMPLEX COMPOUNDS

The present invention relates to a novel process (methodological process) for the preparation of metal complexes, in particular of paramagnetic and/or radioactive chelate complexes, in especially pure form, to the complexes prepared by said process, and to novel chelate complexes with known chelating agents.

Paramagnetic and/or radioactive chelate complexes are used mainly in diagnostic medicine, for example in X-ray, radionuclide, ultrasonic and/or magnetic nuclear resonance diagnostics, as contrast medium. For this utility, it is essential to prepare the chelate complexes in the greatest possible purity. In the known processes of the prior art for the preparation of chelate complexes, an inorganic metal compound, usually a halide, for example a chloride, is reacted with the chelating agent. The complexes so obtained, however, do not have the desired purity. On the contrary, they are contaminated by the counterion present in the inorganic metal compound, by excess or unreacted educt and by products that are formed when neutralising acid, for example hydrohalic acid or sulfuric acid, that forms during the chelation. The neutralisation is necessary, because the chelate complexes used for medicinal purposes must have a physiologically tolerable pH value. The impurities can only be separated with difficulty and incompletely.

It is the object of the present invention to provide a simple process for the preparation of chelate complexes in purer form, wherein the neutralisation step is dispensed with.

The invention relates more particularly to a process for the preparation of a complex of a metal ion and a chelating agent, which comprises transcomplexing a complex of a β-dicarbonyl compound and the said metal ion, which complex is readily soluble in an organic solvent that is not miscible in all proportions with water, with a stoichiometric amount or with a less than equivalent amount of a chelating agent whose binding affinity for the metal ion is greater than that of the β-dicarbonyl compound, or of a salt, preferably a pharmaceutically acceptable salt, of such a chelating agent containing at least one salt-forming group.

The metal ions to be complexed are, in particular, paramagnetic metal ions of the series of the transition metals including the lanthanides and actinides, as well as metal ions of the third main group of the periodic table, and radionuclide ions.

Metal ions of the series of the paramagnetic transition metal ions, exclusive of the lanthanides and actinides, to be singled out for special mention are the iron ions $Fe^{2+}$ and, in particular, $Fe^{3+}$, and also the copper ion $Cu^{2+}$, the cobalt ion $Co^{2+}$, the nickel ion $Ni^{2+}$, the manganese ions $Mn^{2+}$ and $Mn^{3+}$, the chromium ions $Cr^{2+}$ and $Cr^{3+}$ and the vanadinium ion $V^{2+}$.

A particularly suitable metal ion of the series of the lanthanide ions is the gadolinium ion $Gd^{3+}$, but the europium ion $Eu^{2+}$, the lanthanum ion $La^{3+}$ and the ytterbium ion $Yb^{3+}$ may also be mentioned.

A preferred metal ion of the series of the actinides is the protactinium ion $Pa^{4+}$.

Metal ions of the third main group of the periodic table are aluminium ions and, preferably, gallium and indium ions. In the case of gallium and indium the ions of the radioactive isotopes are preferred, for example $^{67}Ga$ and $^{111}In$.

Radionuclide ions are, in particular, the ions of the radioactive isotopes of the above metals, for example of the metastable technetium 99, $^{99m}Tc$, or $^{140}La$, $^{168}Yb$, $^{67}Ga$ or $^{111}In$.

Chelating agents are organic compounds that contain at least two potential ligands, as in particular the desferrioxamines containing free OH groups disclosed, for example, in U.S. Pat. No. 3,634,407, preferably the desferrioxamines of the B-series, most particularly desferrioxamine B commercially available in the form of the methane-sulfonate under the trade name Desferal ®, or derivatives thereof containing an acylated amino group, and also desferrioxamine E. Other preferred chelating agents, especially for $Fe^{3+}$, $Al^{3+}$ and $Cr^{3+}$, are, for example, 2-(3'-hydroxyprid-2'-yl)-3-methyl-3-thiazoline-4-carboxylic acid disclosed in European patent 45 281 and referred to hereinafter as desferrithiocine, and the demethyl derivative thereof also disclosed therein, as well as further siderophores formed from microorganisms, for example rhodotorula acid.

Numerous other chelating agents are suitable, for example 3-hydroxy-2-methyl-4H-pyran-4-one (maltol), (L)-2-amino-3-[3-hydroxypyrid-4-on-1-yl]propionic acid (L-mimosine), and other 3-hydroxy-4-pyridone derivatives, the specific choice of said chelating agents being determined by the desired properties of the chelate complex to be prepared (see below).

Salt-forming groups in a chelating agent are acid groups, for example carboxylic acid, phosphoric acid or sulfonic acid groups, or basic groups, for example amino groups.

Salts of chelating agents which, like desferrithiocine, contain at least one acid group, are preferably alkali metal salts, mainly sodium or potassium salts. Salts of chelating agents which, like desferrioxamin B, contain at least one basic group, are acid addition salts, preferably pharmaceutically acceptable acid addition salts, for example with inorganic acids such as hydrochlorid acid, sulfuric acid or phosphoric acid, or with suitable organic carboxylic or sulfonic acids, for example trifluoroacetic acid or methylsulfonic acid.

A β-dicarbonyl compound is an organic compound which carries two carbonyl groups in 1,3-position to each other and which may also be in enol form, with the proviso that the two carbonyl groups must be available for complexing a metal ion and may not be sterically hindered. A preferred 1,3-dicarbonyl compound is 2,4-pentanedione (acetylacetone), because the acetylacetonates of numerous metals are commercially available.

An organic solvent which is not miscible in all proportions with water is, for example, a suitable carboxylate such as ethyl acetate, a suitable cyclic or, in particular, acyclic ether such as tetrahydrofuran or diethyl ether, or an unsubstituted or halogenated hydrocarbon, for example an aromatic hydrocarbon such as benzene or toluene, an aliphatic hydrocarbon such as pentane or heptane, or a halogenated hydrocarbon such as chloroform or dichloromethane.

In which of the above mentioned solvents a specific metal complex containing a β-dicarbonyl compound is readily soluble depends on the specific complex. Metal acetylacetonates, for example, are readily soluble in ethyl acetate, diethyl ether, benzene or toluene.

The binding affinity of the chelating agent for the metal ion must be sufficiently greater than the binding affinity of the β-dicarbonyl compound for the appropriate metal ion, i.e. the negative decadic logarithm of the disassociation constant (pK) must be greater for the complex consisting of chelating agent and metal ion than for the complex consisting of β-dicarbonyl compound and metal ion, as otherwise the process of this invention will not run or will not proceed quantitatively.

In analogy to the customary naming of the iron(III) complex, the metal complexes of a desferrioxamine will hereinafter be designated as "ferrioxamine", stating the name of the complexed metal and, if necessary, denoting its oxidation state, followed by the suffix "oxamine". By analogy, the complexes formed by desferrithiocine will be named using the suffix "thiocine".

If the chelate complex prepared by the process of this invention is to be used in diagnostic medicine, it must have, for example, the following properties:

Especially if the metal ion in the free form is toxic, the complex must be substantially stable so that as few metal ions as possible will pass into the organism. If the metal ion in question is endogenous and non-toxic in the respective concentration, a lower stability of the complex may be tolerated. As endogenous ions it is preferred to use iron ions for the process of this invention. It goes without saying that the chelate complex as a whole should also be substantially non-toxic and be sufficiently soluble for most uses, and it should also be excreted from the organism as soon as possible after the diagnosis has been performed. The above requirements are admirably fulfilled, for example, by the iron(III) complexes of desferrioxamine B and desferrithiocine.

The process is carried out by adding a solution of the complex of the β-dicarbonyl compound and the metal ion in a suitable solvent in which it is readily soluble, preferably an organic solvent that is immiscible or sparingly miscible with water, for example a suitable ester such as ethyl acetate, or a suitable ether such as diethyl ether, to a solution of the chelating agent in a suitable solvent, and efficiently stirring the mixture. If the solubility of the chelating agent, for example desferrioxamine B mesylate, permits it, the solvent for the chelating agent is conveniently water. If the chelating agent is only sparingly soluble in water, it is also possible to use an aqueous suspension of the chelating agent. The chelating agent can, however, also be used in a non-aqueous solvent, for example an alcohol such as methanol, ethanol or isopropanol. The reactants can be used in equivalent amounts. A small excess, for example 10-20%, of the complex with the β-dicarbonyl compound can also be used. The reaction is preferably carried out in the temperature range from ca. −20° to ca. +150° C., more particularly from 0° to +100° C., preferably from +10° to +70° C., especially from +15° to +40° C. and, most preferably, at room temperature (ca. +20° C.). The reaction temperature in any given case will depend, inter alia, on the melting and boiling points of the solvent or mixture of solvents, on the stability of the reactants and of the chelate complex, and on the desired reaction rate. If desired or necessary, the reaction can be carried out under pressure, for example under the inherent pressure of the system and/or in an inert gas atmosphere, for example under nitrogen or argon. The isolated yields of pure product are ca. 80-100% of theory.

To isolate the desired metal complex and to separate unreacted educt and by-product, i.e. the complex of the β-dicarbonyl compound and the metal ion as well as the liberated β-dicarbonyl compound, use is made of differences in the relative solubility between the desired metal complex and the educt and the by-product. In this connection, it will be expedient to choose for the reaction a solvent system that is suitable for the easy isolation of the desired metal complex.

The complexes with the β-dicarbonyl compound, for example the metal acetylacetonates, are insoluble in water, but are soluble in a substantially water-immiscible solvent such as ethyl acetate or diethyl ether. In contrast, the complexes formed in the process of this invention, for example the desferrioxamine B chelate complexes, are virtually insoluble in at least one substantially water-immiscible organic solvent, for example ethyl acetate, diethyl ether, benzene, toluene or tetrahydrofuran. This virtual insolubility makes it easy to isolate and purify them. The desferrithiocine complexes are preferably prepared in a system consisting of water and a less polar solvent than ethyl acetate, for example diethyl ether.

In the normal case of the reaction mixture containing water, the aqueous phase is separated after completion of the transcomplexing reaction and extracted with an organic solvent in which the desired metal complex has as low a solubility as possible and in which the impurities are as readily soluble as possible. The aqueous phase, if necessary after first concentrating it, is subsequently lyophilised. If, exceptionally, the reaction mixture does not contain water, it is strongly concentrated, for example to dryness, and the residue is then extracted with an organic solvent in which the desired metal complex has as low a solubility as possible and in which the impurities are as readily soluble as possible.

The complexes with the β-dicarbonyl compound are commercially available, for example numerous acetylacetonates, or they can be prepared in a manner known per se, for example by reacting the β-dicarbonyl compound with a salt of the corresponding metal, for example a chloride. It is also possible to react metal salts of 2-ethylcaproic acid (octoates), metal naphthenates or metal stearates with the β-dicarbonyl compound [G. Stöckelmann et al., Angew. Chem. 79, 530 (1967)] or to bring cation exchangers charged with the desired metal ion, in an organic solvent, into contact with the β-dicarbonyl compound [K. Ohzeki et al., Bull. Chem. Soc. Jap. 48, 67-68 (1975)].

A preferred embodiment of the process of this invention comprises transcomplexing an acetylacetonate of a radionuclide ion or of a paramagnetic metal ion selected from the series of the transition metals, including the lanthanides, preferably an acetylacetonate of $Fe^{2+}$, $Fe^{3+}$, $Cu^{2+}$, $Co^{2+}$, $Ni^{2+}$, $Mn^{2+}$, $Mn^{3+}$, $Cr^{2+}$, $Cr^{3+}$, $V^{2+}$, $Gd^{3+}$, $Eu^{2+}$, $La^{3+}$ or $Yb^{3+}$, with a chelating agent selected from desferrioxamine B, desferrioxamine E and desferrithiocine and a pharmaceutically acceptable salt thereof.

Another preferred embodiment of the process of this invention comprises reacting an acetylacetonate of iron(III), manganese(III), indium(III) or gallium(III) with desferrioxamine B, desferrioxamine E, desferrithiocine, maltol, L-mimosine, 3-hydroxy-1,2-dimethyl-4-pyridone, 3-hydroxy-2-methyl-N-propyl-4-pyridone or rhodotorula acid in water/ethyl acetate or water/diethyl ether at room temperature.

The invention also relates to the chelate complexes obtained by the process of this invention, to novel chelate complexes, i.e. those not belonging to the prior art, especially the novel chelate complexes described in the Examples, and to the use of said chelate complexes in diagnostic medicine.

The chelate complexes containing radioactive metal ions, for example $^{99m}Tc$, $^{111}In$, $^{67}Ga$, $^{140}La$ or $^{168}Yb$, can be used, for example, as radiopharmaceuticals. Chelate complexes with stable isotopes that have a higher atomic weight than iodine absorb X-rays and can therefore be used as X-ray contrast media. A number of these last mentioned chelate complexes absorb, reflect or scatter ultrasonic waves and hence can also be used in ultrasonic diagnosis. Chelate complexes that contain a paramagnetic metal ion, for example $Gd^{3+}$, $Mn^{2+}$, $Cr^{3+}$ or $Fe^{3+}$, with symmetrical electronic ground state, accelerate the spin relaxation and can be used in NMR spectroscopy as contrast media. Chelate complexes that contain a paramagnetic metal ion with unsymmetrical electronic ground state can be used in NMR spectroscopy or in magnetic in vivo resonance spectroscopy as displacement reagents. Aluminium complexes can be used as reference compounds for the evaluation (for example toxicity studies) of chelating agents.

The dose to be administered to a mammal will depend, inter alia, on the chelate complex, on the nature of the mammal, and on the envisaged use, and is, for example, in the order of 0.001-1 millimole per kilogram of body weight. Administration is preferably made parenterally, more particularly intravenously, or enterally, for example orally.

The invention is illustrated by the following non-limitative Examples.

ABBREVIATIONS

DMSO: dimethyl sulfoxide
FAB: fast atom bombardment
HPLC: high pressure liquid chromatography

EXAMPLE 1

With efficient stirring, a solution of 3.38 kg (5.15 mol) of deferrioxamine B mesylate in 20 liters of water is added at room temperature to a solution of 2.20 kg (5.66 mol) of commercial iron(III) acetylacetonate in 25 liters of ethyl acetate. The mixture is stirred efficiently for 1 hour and turns red immediately. The aqueous phase is extracted with 4×10 liters of ethyl acetate, then concentrated somewhat at 55° C. and 85 000 Pa (0.85 bar) to remove residual ethyl acetate, and thereafter lyophilised. The lyophilisate is digested with ethyl acetate and dried under a high vacuum, affording 3.54 kg (98% of theory) of deep red, hygroscopic ferrioxamine B mesylate that contains 1 mol of water.

$C_{25}H_{45}FeN_6O_8 \cdot CH_3SO_3H \cdot H_2O$ (727.633): Cal: C 42.92, H 7.06, Fe 7.68, N 11.55, S 4.41. Found C 43.15, H 7.19, Fe 7.81, N 11.60, S 4.44.

HPLC: column: Hypersil ODS, 5 μm, 120×4.6 mm systems: solution A=2.5 mmol of phosphate buffer pH 3.0 solution B=20% of solution A and 80% of acetonitrile

| | Gradient: | | |
|---|---|---|---|
| Minutes | % A | % B | flow: ml/min |
| 0 | 100 | 0 | 2.3 |
| 10 | 70 | 30 | 2.3 |
| 12 | 0 | 100 | 2.3 |
| 15 | 100 | 0 | 2.3 |

$R_f$ value: 7 minutes,

Mass spectrum [(+) FAB in thioglycerol]: $(M+H)^+ = 614$.

EXAMPLE 2

With efficient stirring, 16.80 g (48 mmol) of manganese(III) acetylacetonate are added to 26.40 g (40 mmol) of desferrioxamine B mesylate in 400 ml of water and the mixture is efficiently stirred for 2 hours at room temperature. Working up as in Example 1 gives a deep green, slightly hygroscopic manganese(III) oxamine B mesylate that contains 0.5 mol of water.

$C_{25}H_{45}MnN_6O_8 \cdot CH_3SO_3H \cdot \frac{1}{2}H_2O$ (717.708): Cal. C 43.51, H 7.02, N 11.71, S 4.46, Mn 7.66. Found: C 43.38, H 7.02, N 11.50, S 4.29, Mn 8.16.

HPLC (conditions as in Example 1): $R_f$ value=5.5 minutes

Solubilities: readily soluble in water.

EXAMPLE 3

In accordance with the procedure described in Example 2, but stirring for only 1 hour and digesting the lyophilisate with diethyl ether/n-heptane, white, hygroscopic aluminiumoxamine B mesylate that contains 1.5 mol of water is obtained from 13.12 g (20 mmol) of desferrioxamine B mesylate in 250 ml of water and 7.78 g (24 mmol) of aluminium acetylacetonate in 200 ml of ethyl acetate.

$C_{25}H_{45}AlN_6O_8 \cdot CH_3SO_3H \cdot 1,5H_2O$ (707.773): Cal: C 44.12, H 7.40, N 11.87, S 4.53, Al 3.81. Found: C 44.11, H 7.29, N 11.65, S 4.47, Al 3.70.

HPLC (conditions as in Example 1): $R_f$ value=7 minutes.

Solubilities: readily soluble in water.

EXAMPLE 4

In accordance with the procedure of Example 3, but without digestion of the lyophilisate with diethyl ether/n-heptane, white, slightly hygroscopic indiumoxamine B mesylate is obtained from 6.56 g (10 mmol) of desferrioxamine B mesylate in 100 ml of water and 4.94 g (12 mmol) of indium(III) acetylacetonate in 100 ml of ethyl acetate.

$C_{25}H_{45}InN_6O_8 \cdot CH_3SO_3H$ (768.593): Cal. C 40.63, H 6.43, N 10.93. Found: C 40.50, H 6.40, N 10.90.

Mass spectrum [(+) FAB, thioglycerol]: $(M+H)^+ = 673$.

HPLC: column: Hypersil ODS, 5 μm, 120×4.6 mm. systems: solution A=2.5 mmol of phosphate buffer pH 3.0; solution B=20% of solution A and 80% of acetonitrile.

| | Gradient: | | |
|---|---|---|---|
| Minutes | % A | % B | flow: ml/min |
| 0 | 100 | 0 | 2.3 |
| 10 | 60 | 40 | 2.3 |
| 12 | 0 | 100 | 2.3 |
| 15 | 100 | 0 | 2.3 |

$R_f$ value: 9 minutes,
Solubilities: readily soluble in water and DMSO.

EXAMPLE 5

In accordance with the procedure described in Example 4, white, slightly hygroscopic galliumoxamine B mesylate is obtained from 3.28 g (5 mmol) of desferrioxamine B mesylate in 50 ml of water and 2.20 g (6 mmol) of gallium(III) acetylacetonate in 50 ml of ethyl acetate.

$C_{25}H_{45}GaN_6O_8 \cdot CH_3SO_3H$ (723.493): Cal. C 43.16, H 6.83, N 11.62. Found C 43.1, H 6.8, N 11.5.

Mass spectrum [(+) FAB, thioglycerol]: $(M+H)^+ = 627$.

HPLC (conditions as in Example 4): $R_f$-value = 7.3 minutes.

Solubilities: in water—30%, in DMSO—20%, in polyethylene glycol 400—2%.

EXAMPLE 6

A solution of 5.29 g (15 mmol) of iron(III) acetylacetonate in 300 ml of ethyl acetate is added to a suspension of 5.26 g (10 mmol) of desferrioxamine E in 500 ml of water, and the mixture is efficiently stirred for 5 hours at room temperature. The aqueous phase is then extracted repeatedly with ethyl acetate and then lyophilised to give ferrioxamine E.

HPLC (conditions as in Example 11): $R_f$-value = 3.92 minutes (educt: 4.70 minutes).

$C_{27}H_{45}FeN_6O_9 \cdot 2,5H_2O$ (698.58): Cal: C 46.42, H 7.21, Fe 7.99, N 12.03. Found: C 46.35, H 7.15, Fe 8.02, N 11.77.

Mass spectrum [(+) FAB in thioglycerol]: $(M+H)^+ = 654$.

Solubility: in water 30%, in DMSO 20%, in polyethylene glycol 400 2%.

EXAMPLE 7

In accordance with the procedure described in Example 6, ferrithiocine is obtained from a suspension of 4.76 g (20 mmol) of desferrithiocine (free acid) in 200 ml of water and 7.00 g (20 mmol) of manganese(III) acetylacetonate in 300 ml of ethyl acetate after stirring for 6 hours.

$R_f$-value = 0.50 (methylene chloride/methanol/water = 130:50:8), for comparison: $R_f$ of desferrithiocine = 0.40.

Solubility: readily soluble in water.

EXAMPLE 8

In accordance with the procedure of Example 7, green manganese thiocine is obtained from a suspension of 4.76 g (20 mmol) of desferrithiocine (free acid) in 200 ml of water and 7.00 g (20 mmol) of manganese(III) acetylacetonate in 300 ml of ethyl acetate.

$R_f = 0.45$ (methylene chloride/methanol/water = 130:50:8) for comparison: $R_f$ of desferrithiocine = 0.40.

EXAMPLE 9

14.10 g (40 mmol) of iron(III) acetylacetonate in 400 ml of diethyl ether are added to a suspension of 9.52 g (40 mmol) of desferrithiocine and 10.41 g (40 mmol) of desferrithiocine sodium salt in 400 ml of water, and the mixture is efficiently stirred for 1 hour at room temperature. The red aqueous phase is extracted repeatedly with diethyl ether and then lyophilised to give ferrithiocine sodium salt.

$C_{20}H_{16}FeN_4NaO_6S_2 \cdot 2H_2O$ (587.369): Cal: C 40.90, H 3.43, N 9.54, S 10.92. Found: C 41.12, H 3.47, N 9.66, S 11.15.

EXAMPLE 10

5.29 g (15 mmol) of iron(III) acetylacetonate in 500 ml of ethyl acetate are added to a suspension of 3.78 g (30 mmol) of 3-hydroxy-2-methyl-4-pyrone (maltol) in 500 ml of water, and the mixture is efficiently stirred for 3 hours at room temperature. The aqueous phase is then extracted repeatedly with ethyl acetate and thereafter lyophilised to give the iron(III) maltol complex.

$C_{18}H_{15}FeO_9$ (431.163): Cal: C 49,96, H 3.57, Fe 12.91, $H_2O$ 0.37. Found: C 49,77, H 3.64, Fe 13.10, $H_2O$ 0.37.

HPLC (conditions as in Example 1, but gradient after 14 minutes, 100% of A and 0% of B): 4.85 minutes (educt: 3.75 minutes), solubilities: 10% in DMSO, 3% in water.

EXAMPLE 11

3.2 g (9 mmol) of iron(III) acetylacetonate in 200 ml of ethyl acetate are added to a suspension of 1.5 g (7.5 mmol) of L-mimosine [(L)-2-amino-3-[3-hydroxypyrid-4-on-1-yl]propionic acid q.v. The Merck Index, 10th Edition, monograph number 6065] in 500 ml of water, and the mixture is efficiently stirred for 3 hours at room temperature. The aqueous phase is then extracted repeatedly with altogether 2000 ml of ethyl acetate and then lyophilised to give the iron(III) mimosine complex.

$C_{24}H_{27}FeN_6O_{12} \cdot 2H_2O$ (683.393): Cal: C 42.18, H 4.57, N 12.30. Found: C 41.95, H 4.56, N 12.00.

HPLC (apart from the gradients given below, the conditions are as indicated in Example 1):

| | Gradient: | | |
| Minutes | % A | % B | flow: ml/min |
| --- | --- | --- | --- |
| 0 | 100 | 0 | 2.3 |
| 12 | 0 | 100 | 2.3 |
| 14 | 100 | 0 | 2.3 |
| 15 | 100 | 0 | 2.3 |

$R_f$-value: 0.54 minutes (educt: 0.62 minutes)
Solubility: ca. 5% in water.

EXAMPLE 12

5.29 g (15 mmol) of iron(III) acetylacetonate in 300 ml of ethyl acetate are added to a suspension of 4.17 g (30 mmol) of 3-hydroxy-1,2-dimethyl-4-pyridone (described in European patent 93 498, Example 3) in 300 ml of water, and the mixture is efficiently stirred for 3 hours at room temperature. The aqueous phase is then extracted repeatedly with ethyl acetate and subsequently lyophilised. For further purification, the lyophilisate is digested in 300 ml of ethyl acetate to give the iron(III)-3-hydroxy-1,2-dimethyl-4-pyridone complex.

$C_{21}H_{24}FeN_3O_6 \cdot 1,3H_2O$ (493.709): Cal: C 51.09, H 5.43, N 8.51. Found: C 51.03, H 5.38, N 8.34.

HPLC (conditions as in Example 11): $R_f = 4.10$ minutes (educt: 13.63 minutes).

Solubility: 10% in DMSO, 20% in water.

EXAMPLE 13

4.3 g (12 mmol) of iron(III) acetylacetonate in 40 ml of ethyl acetate are added to 2.0 g (10 mmol) of 3-hydroxy-2-methyl-N-propyl-4-pyridone hydrochloride (described in European patent 93 498, Example 4) in 400 ml of water, and the mixture is efficiently stirred for 3 hours at room temperature. The aqueous phase is then extracted repeatedly with altogther 3000 ml of ethyl acetate and subsequently lyophilised to give the iron-(III)-3-hydroxy-2-methyl-N-propyl-4-pyridone hydrochloride complex.

HPLC (conditions as in Example 1): $R_f = 6.51$ minutes (educt: 6.33 minutes)
Solubility: 10% in DMSO, 20% in water.

EXAMPLE 14

In accordance with the procedure described in Example 12, 3.44 g (10 mmol) of rhodotorula acid (sold by Sigma Chem. Company, P.O. Box 14508, St. Louis, Mo., USA) in 500 ml of water are reacted with 3.53 g (10 mmol) of iron(III) acetylacetonate in 500 ml of ethyl acetate. Working up as described in Example 12 gives the iron(III) rhodotorula acid complex.

$C_{42}H_{66}Fe_2N_{12}O_{18} \cdot 1H_2O$ (1156.77): Cal: C 43.61, H 5.93, N 14.53. Found: C 43.68, H 5.84, N 14.41.

HPLC (conditions as in Example 11): $R_f = 1.22$ minutes (educt: 3.22 minutes)

Solubility: 10% in DMSO, 5% in water.

What is claimed is:

1. A process for the preparation of a complex of a metal ion and a chelating agent, said metal ion being able to be complexed by a β-dicarbonyl compound, which comprises transcomplexing a complex of a β-dicarbonyl compound and said metal ion, which complex is readily soluble in an organic solvent that is not miscible in all proportions with water, with a stoichiometric amount or a less than equivalent amount of a chelating agent whose binding affinity for the metal ion is greater than that of the β-dicarbonyl compound, or of a salt of such a chelating agent containing at least one salt-forming group.

2. A process according to claim 1, wherein the metal ion is a paramagnetic metal ion selected from the series of the transition metals, including the lanthanides.

3. A process according to claim 1, wherein the metal ion is an iron(III) ion.

4. A process according to claim 1, wherein the metal ion is a radionuclide ion.

5. A process according to claim 1, wherein the chelating agent is desferrioxamine B or a pharmaceutically acceptable acid addition salt thereof.

6. A process according to claim 1, wherein the chelating agent is desferrioxamine E or a pharmaceutically acceptable salt thereof.

7. A process according to claim 1, wherein the chelating agent is desferrithiocine or a pharmaceutically acceptable salt thereof.

8. A process according to claim 1, wherein an acetylacetonate of the metal ion is reacted with the chelating agent.

9. A process according to claim 1, which comprises transcomplexing an acetylacetonate of a radionuclide ion or of a paramagnetic metal ion selected from the series of the transition metals, including the lanthanides, with a chelating agent selected from desferrioxamine B, desferrioxamine E and desferrithiocine and a pharmaceutically acceptable salt thereof.

10. A process according to claim 9, which comprises transcomplexing an acetylacetonate of an ion selected from $Fe^{2+}$, $Fe^{3+}$, $Cu^{2+}$, $Co^{2+}$, $Ni^{2+}$, $Mn^{2+}$, $Mn^{3+}$, $Cr^{2+}$, $Cr^{3+}$, $V^{2+}$, $Gd^{3+}$, $Eu^{2+}$, $La^{3+}$ and $Yb^{3+}$.

11. A process according to claim 1, wherein the reaction is carried out in a system consisting of water and a water-immiscible or substantially water-immiscible organic solvent, with efficient stirring, in the temperature range from $+15°$ to $+40°$ C.

12. A process according to claim 11, wherein the organic solvent is ethyl acetate or diethyl ether.

13. A process according to claim 11, wherein the desired metal complex is isolated from the reaction mixture by first separating the aqueous phase and extracting it with an organic solvent in which the desired metal complex has as low a solubility as possible and in which the impurities are as readily soluble as possible, and then lyophilising the aqueous phase.

14. A process according to claim 9, wherein the reaction is carried out in a system consisting of water and a water-immiscible or substantially water-immiscible organic solvent, with efficient stirring, in the temperature range from $+15°$ to $+40°$ C.

* * * * *